(12) United States Patent
Martin

(10) Patent No.: US 6,419,817 B1
(45) Date of Patent: *Jul. 16, 2002

(54) DYNAMIC OPTIMIZATION OF CHEMICAL ADDITIVES IN A WATER TREATMENT SYSTEM

(75) Inventor: Roy Martin, Downers Grove, IL (US)

(73) Assignee: United States Filter Corporation, Palm Desert, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/603,765

(22) Filed: Jun. 22, 2000

(51) Int. Cl.$^7$ .......................... G01N 17/02; G01N 17/04

(52) U.S. Cl. ..................... 205/775.5; 204/404; 324/700

(58) Field of Search ...................... 204/404; 205/775.5, 205/791, 776.5, 777; 324/700

(56) References Cited

U.S. PATENT DOCUMENTS

| | | |
|---|---|---|
| 2,008,684 A | 7/1935 | Craddock |
| 2,212,260 A | 8/1940 | Brothman |
| 2,249,263 A | 7/1941 | Wheelwright, Jr. |
| 2,268,461 A | 12/1941 | Nichols |
| 2,556,014 A | 6/1951 | Tolman |
| 2,651,582 A | 9/1953 | Courtney |
| 2,686,110 A | 8/1954 | Carver |
| 2,740,696 A | 4/1956 | Longwell |
| 3,252,689 A | 5/1966 | Blomgren, Sr. et al. |
| 3,319,937 A | 5/1967 | Wilson et al. |
| 3,389,970 A | 6/1968 | Scheibel |
| 3,536,646 A | 10/1970 | Hatch et al. |
| 3,559,959 A | 2/1971 | Davis et al. |
| T896,051 I4 | 3/1972 | Hamlin et al. |
| 3,702,298 A | 11/1972 | Zsoldos et al. |
| 3,742,735 A | 7/1973 | Verreyne et al. |
| 3,747,809 A | 7/1973 | Latinen et al. |
| 3,756,570 A | 9/1973 | Bühner |
| 3,852,234 A | 12/1974 | Venema |
| 4,016,078 A | 4/1977 | Clark |
| 4,113,688 A | 9/1978 | Pearson |
| 4,125,574 A | 11/1978 | Kastner et al. |

(List continued on next page.)

FOREIGN PATENT DOCUMENTS

| | | |
|---|---|---|
| EP | 0 257 740 | 3/1988 |
| LU | 80951 | 2/1979 |

OTHER PUBLICATIONS

Kim, Yong H., "On the Activation of Polymeric Flocculants," AIChE Annual Spring Meeting, Houston, TX, Apr. 2–6, 1989.

U.S. Filter/Stranco, "Ryznar Stability Index The $3^{rd}$ Dimension Needed for Proper 'Water Balance,'" Aquatic Technology Newsletter, vol. 1, No. 1, pp. 1–3.

U.S. Filter/Stranco, "Ryznar Dissolved Solids, Friend or Foe?", Aquatic Technology Newsletter, vol. 1, No. 2, 1988; pp. 1–7.

U.S. Filter/Stranco, "The Relationship of ORP to PPM and Its Automated Control," Aquatic Technology Newsletter, vol. 1, No. 3, 1999, pp. 1–5.

(List continued on next page.)

Primary Examiner—Robert J. Warden, Sr.
Assistant Examiner—Kaj K. Olsen
(74) Attorney, Agent, or Firm—Wolf, Greenfield & Sacks, P.C.

(57) ABSTRACT

The present invention describes an apparatus for the optimized control of various treatment chemicals (inhibitors) applied for corrosion and/or deposit inhibition. The apparatus consist of a microprocessor system that controls inhibitor concentrations as a result of processed inputted data. The inputted data includes, but is not limited to values consistent with the monitoring of Electrochemical Noise, Linear Polarization Rate, heat transfer, concentrations of water treatment chemistry, critical water chemistry parameters, and critical operational characteristics.

8 Claims, 8 Drawing Sheets

U.S. PATENT DOCUMENTS

| | | |
|---|---|---|
| 4,146,676 A | 3/1979 | Saeman et al. |
| 4,171,166 A | 10/1979 | Trowbridge et al. |
| 4,217,145 A | 8/1980 | Gaddis |
| 4,218,147 A | 8/1980 | Rosenberger |
| 4,233,265 A | 11/1980 | Gasper |
| 4,243,636 A | 1/1981 | Shiraki et al. |
| 4,433,701 A | 2/1984 | Cox et al. |
| 4,470,907 A | 9/1984 | Seneza |
| 4,522,502 A | 6/1985 | Brazelton |
| 4,550,011 A | 10/1985 | McCollum |
| 4,575,678 A * | 3/1986 | Hladky ...................... 204/404 |
| 4,648,043 A | 3/1987 | O'Leary |
| 4,664,528 A | 5/1987 | Rodgers et al. |
| 4,701,055 A | 10/1987 | Anderson |
| 4,719,252 A | 1/1988 | Dutton et al. |
| 4,747,978 A | 5/1988 | Loehr et al. |
| 4,752,740 A | 6/1988 | Steininger |
| 4,965,016 A | 10/1990 | Saitoh et al. |
| 4,977,292 A | 12/1990 | Hwa et al. |
| 5,004,549 A | 4/1991 | Wood et al. |
| 5,018,871 A | 5/1991 | Brazelton et al. |
| 5,061,456 A | 10/1991 | Brazelton et al. |
| 5,112,521 A | 5/1992 | Mullins et al. |
| 5,130,033 A | 7/1992 | Thornhill |
| 5,135,968 A | 8/1992 | Brazelton et al. |
| 5,139,627 A * | 8/1992 | Eden et al. ................. 204/404 |
| 5,164,429 A | 11/1992 | Brazelton et al. |
| 5,213,694 A | 5/1993 | Craig |
| 5,239,257 A | 8/1993 | Muller et al. |
| 5,306,432 A | 4/1994 | Puetz |
| 5,316,031 A | 5/1994 | Brazelton et al. |
| 5,332,511 A | 7/1994 | Gay et al. |
| 5,382,367 A | 1/1995 | Zinkan et al. |
| 5,494,588 A | 2/1996 | LaZonby et al. |
| 5,658,467 A | 8/1997 | LaZonby et al. |
| 5,683,654 A | 11/1997 | Dallmier et al. |
| 5,785,867 A | 7/1998 | LaZonby et al. |
| 5,800,732 A | 9/1998 | Coughlin et al. |
| 5,814,233 A | 9/1998 | Starkey et al. |
| 5,820,256 A | 10/1998 | Morrison |
| 5,849,985 A | 12/1998 | Tieckelmann et al. |
| 5,858,249 A | 1/1999 | Higby |
| 5,882,526 A | 3/1999 | Brown et al. |
| 5,888,374 A * | 3/1999 | Pope et al. ............... 205/775.5 |
| 5,902,751 A | 5/1999 | Godec et al. |
| 5,947,596 A | 9/1999 | Dowd |
| 5,972,196 A | 10/1999 | Murphy et al. |
| 5,980,758 A | 11/1999 | LaZonby et al. |
| 6,015,484 A * | 1/2000 | Martinchek et al. ..... 205/775.5 |
| 6,030,842 A | 2/2000 | Peacny-Stoner |
| 6,045,706 A | 4/2000 | Morrison et al. |
| 6,068,012 A * | 5/2000 | Beardwood et al. ........... 137/3 |
| 6,132,593 A * | 10/2000 | Tan ......................... 205/776.5 |
| 6,143,184 A | 11/2000 | Martin et al. |
| 6,146,538 A | 11/2000 | Martin |
| 6,149,819 A | 11/2000 | Martin et al. |

OTHER PUBLICATIONS

U.S. Filter/Stranco, "The Chemistry and Control of Chloramines," Aquatic Technology Newsletter, vol. 1, No. 4, 1999, pp. 1–5.

U.S. Filter/Stranco, "Yes, Your Pool Needs Calcium Too," Aquatic Technology Newsletter, vol. 1, No. 5, pp. 1–3.

U.S. Filter/Stranco, "Why Do I Have Algae In My Pool?" Aquatic Technology Newsletter, vol. 1, No. 5, pp. 1–3.

Carpenter, Colleen et al., "Chlorine Disinfection of Recreational Water for *Cryptosporidium parvum,*" Emerging Infectious Diseases, vol. 5, No. 4, Jul.–Aug. 1999, pp. 579–584.

U.S. Filter/Stranco, "ECS–Pool (w/CHF–150) Engineering Packet," Apr. 22, 1999.

Kowalsky, L., "Pool–Spa Operators Handbook," National Swimming Pool Foundation, 1983–1990.

Lynntech, Inc., "Electrochemical Ozone Generator," Model 124 Product Literature (date unknown).

U.S. Filter/Stranco, "Strantrol Automated Water Chemistry Control for Commercial Pools," 1998.

U.S. Filter/Stranco, "Strantrol System 3 Pool & Spa Chemistry Controller," 2000.

U.S. Filter/Stranco, "Strantrol System 4 Pool & Spa Chemistry Controller," 2000.

U.S. Filter/Stranco, "Strantrol System5F Pool & Spa Chemistry Controller," 2000.

U.S. Filter/Stranco, "Strantrol System6 Pool Chemistry & Filter Backwash Controller," 2000.

U.S. Filter/Stranco, "Strantrol System7 Mechanical Room Controller for Aquatic Facilities," 2000.

Kloberdanz, B., "The Air in There: Enhancing an Indoor Pool Environment," Recreation Management, 2000.

Selvick, E., "Take Control of 'Yo–Yo' Treatment Cycles," International Aquatics, National Trade Publications, Inc., Jul./Aug. 1997.

Frazier, B., "Automation to the Rescue," Aquatics International, May/Jun. 1998.

Batt, T. et al., "The Water Down Under," Parks & Recreation, Nov. 1999.

Krone, D., "Automated Water Chemistry Control at University of Virginia Pools," Facilities Manager, vol. 13, No. 6, Nov./Dec. 1997.

U.S. Filter/Stranco, "Remote Monitoring for Unstaffed Pools," Parks & Recreation, Nov. 1997.

Minton, E., "On the Waterpark," Swimming Pool/Spa Age (date unknown).

U.S. Filter/Stranco, "Environmental Control at Indoor Pool: New ECS System Eliminates Chronic Air Quality Woes For New York School District Pool," Stranco Products Capsule Case History #806, Jul. 1998.

U.S. Filter/Stranco, "Environmental Control at Indoor Pool Complex: New ECS System Optimizes Air & Water Quality at Colorado Recreation Center," Stranco Products Capsule Case History #807, Nov. 1998.

U.S. Filter/Stranco, "Environmental Control at Indoor Pool: Parks District Uses New ECS System to Eliminate Chronic Air Quality Problems at High School Pool," Stranco Products Capsule Case History #808, May 1999.

U.S. Filter/Stranco, "Environmental Control at Indoor Pool: ECS System Optimizes Air & Water Quality at Texas School District Swim Center," Stranco Products Capsule Case History #811, Nov. 1999.

U.S. Filter/Stranco, "Environmental Control at Special Indoor Pool: New ECS System Eliminates Chronic Air Quality Woes in School District Pool & Spa Serving Special Needs Children," Stranco Products Capsule Case History #812, Oct. 1999.

U.S. Filter/Stranco, "Environmental Control at Indoor Pool: ECS System Eliminates Chronic Air Quality Problems at High School and Parks District Indoor Pool Facility," Stranco Products Capsule Case History #813, Jul. 2000.

U.S. Filter/Stranco, "Environmental Control at Indoor Pool: ECS System Optimizes Air & Water Quality at Iowa Recreation Center," Stranco Products Capsule Case History #814, May 2000.

U.S. Filter/Stranco, "Air & Water Quality Control for Indoor Aquatic Facilities," U.S. Filter Corporation, 1998.

U.S. Filter/Stranco, "Strantrol ECS—Environmental Control System (For Pool)," 2000.

U.S. Filter/Stranco, "Abstracts of Strancol ECS Case Histories," (date unknown).

Williams, K., "Aquatic Facility Operator Manual," National Recreation and Park Association, Second Edition, 1995.

Normenausschusse Wasserwesen, "Treatment and disinfection of water used in bathing facilities," DIN 19643-3, Feb. 1999.

Normenausschusse Wasserwesen, "Treatment and disinfection of water used in bathing facilities," DIN 19643-3, Apr. 1997.

Normenausschusse Wasserwesen, "Treatment and disinfection of water used in bathing facilities," DIN 19643-2, Apr. 1997.

Normenausschusse Wasserwesen, "Treatment and disinfection of water used in bathing facilities," DIN 19643-1, Apr. 1997.

Stranco, "The Best of Poolfax," The Poolfax Newsletter, 1981-1984.

Victorin et al., "Redox potential measurements for determining the disinfecting power of chlorinated water," *J. Hyg., Camb.*, 70, 1972, pp. 313-323.

U.S. Filter/Stranco, "Environmental Control System Training Meeting, Mar. 15, 2000".

Kim, Yong H., "Evaluation of Redox Potential and Chlorine Residual as a Measure of Water Disinfection," presented at the 54th International Water Conference, Pittsburgh, PA, Oct. 11-13, 1993.

Scully et al., Disinfection Interference in Wastewaters by Natural Organic Nitrogen Compounds, *Environ. Sci. Techn.*, vol. 30, No. 5, 1996, pp. 1465-1471.

White, Geor. Clifford, Handbook of Chlorination and Alternative Disinfectants, Third Edition, (date unknown), pp. 801, 803-809, 922-924.

Carlson, S., "Fundamentals of water disinfection," *J Water SRT—Aqua*, vol. 40, No. 6, (1991), pp. 346-356.

Lund, E., "Oxidative Inactivation of Poliovirus," from the Virological Laboratory of the Department of Bacteriology, University of Gothenburg, and the Virological Department of the Municipal Laboratories, Gothenburg, Sweden, Springer-Verlag, (1963), pp. 1-49.

Lund et al., "The Effect of Oxidation and Reduction on the Infectivity of Poliomyelitis Virus," from the Virological Laboratory of the Department of Bacteriology, University of Gothenburg, and the Virological Department of the Municipal Laboratories, Gothenburg, Sweden, Springer-Verlag, (1961), pp. 100-110.

Lund, E., "Inactivation of Poliomyelitis Virus by Chlorination at Different Oxidation Potentials," from the Virological Laboratory of the Department of Bacteriology, University of Gothenburg, and the Virological Department of the Municipal Laboratories, Gothenburg, Sweden, Springer-Verlag, (1961), pp. 330-342.

Lund, E., "The Significance of Oxidation in Chemical Inactivation of Poliovirus," from the Virological Laboratory of the Department of Bacteriology, University of Gothenburg, and the Virological Department of the Municipal Laboratories, Gothenburg, Sweden, Springer-Verlag, (1963), pp. 1-13.

Lund, E., "The Rate of Oxidative Inactivation of Poliovirus and its Dependence on the Concentration of the Reactants," from the Virological Laboratory of the Department of Bacteriology, University of Gothenburg, and the Virological Department of the Municipal Laboratories, Gothenburg, Sweden, Springer-Verlag, (1963), pp. 1-18.

Stranco, "Solutions: Effluent Dechlorination", Stranco Product Literature (date unknown).

Hensley, R. et al., "Disinfection Metamorphosis: From Chemicals to Control," *Operations Forum*, vol. 12, No. 4, Apr. 1995.

Hetzler, J.T. et al., "ORP: A Key to Nutrient Removal," *Operations Forum*, vol. 12, No. 2, Feb. 1995.

Bossard, G. et al., "Optimizing Chlorination/Dechlorination at a Wastewater Treatment Plant," reprinted from *Public Works*, Jan. 1995.

Eddington, Gordon, "Successfully Managing Wastewater Chlorination," Stranco Product Literature (date unknown).

Ryan, D. et al., "Waste Not, Want Not: Avoiding Chemical Excesses," reprinted from *Operations Forum*, vol. 11, No. 4, Apr. 1994.

D'Adam, D. et al., "A Case Study of Wastewater Plant Disinfection," reprinted from *Public Works Magazine*, Nov., 1994.

"Louisiana Plant Uses New Technology for Dechlorination," reprinted from *American City & County*, Feb. 1994.

Kiser, P. et al., "ORP or Residual: Which Measures Oxidation?" Sep. 10, 1992, pp. 1-7.

"Aquasol Controllers: Chemical Automation for Pools and Spas," Product Literature (date unknown).

"Pool and Spa Controller: Acu-200 Pool Management Software," Product Literature (date unknown).

"Acu-Trol Programmable Controllers," Product Literature from www.acu-trol.com, printed Nov. 19, 1999.

Santa Barbara Control Systems, "Chemtrol™ PC Programmable Controllers: Integrated Water Treatment with Remote Control," Product Literature, (date unknown).

"Chemical Automatic Pool Controllers," Product Literature from www.sbcontrol.com, printed Nov. 19, 1999.

"Chemical—PC6000 Controller," Product Literature from www.sbcontrol.com, printed Nov. 19, 1999.

"Chemtrol—PC3000 Controller," Product Literature from www.sbcontrol.com, printed Nov. 19, 1999.

"AK100 Swimming Pool Control Systems," Product Literature from www.acu-trol.com, printed Nov. 19, 1999.

ACU-TROL, "AK100 Series" Product Literature (date unknown).

ACU-TROL, "Acu-Trol Programmable Controllers: AK100 Series and AK200," Product Literature (date unknown).

Aquasol Controllers, Inc., "Aquasol WTC," Product Literature, (date unknown).

Aquasol Controllers, Inc., "What is a Controller?" Product Literature from www.aquasol.com, printed Nov. 19, 1999.

Aquasol Controllers, Inc., "Aquasol WTC Specifications," Product Literature from www.aquasol.com, printed Nov. 19, 1999.

Aquasol Controllers, Inc., "Aquasol SPC Specifications," Product Literature from www.aquasol.com, printed Nov. 19, 1999.

ACU-TROL, "AK100 Summary," Product Literature from www.acu-trol.com, printed Nov. 19, 1999.

Cat Controllers, "Cat 2000+ Programmable Water Chemistry Controller," Product Literature (date unknown).

ROLA–ChEM Corporation, "The New Wave in Water Management: Take Control with Rola–Chem," Product Catalog, Apr. 1999.

Strand, R. et al., "ORP As a Measure of Evaluating and Controlling Disinfection in Potable Water," (Source and date unknown).

Mansfeld et al "Electrochemical Noise Analysis of Iron Exposed to NaCl Solutions of Different Corrositivity", J. Electrochem. Soc. 140, pp. 2205–2209, 1993.*

Brusamarello et al. "Analysis of Different Methods to Calculate Electrochemical Noise Resistance Using a Three –Electrode Cell", Corrosion, 55, pp. 273–282, 2000.*

Eden, Comments on Mansfeld et al (J. Electrochem. Soc. 140, pp. 2205–2209, 1993), J. Electrochem. Soc. 141, pp. 1402–1404, 1994.*

* cited by examiner-

TYPICAL INSTALLATION (BASIC TOWER APPLICATION)

DYNAMIC OPTIMIZATION OF CHEMICAL ADDITIVES IN A WATER TREATMENT SYSTEM

FIELD OF THE INVENTION

This invention relates to the addition of chemical additives to a water treatment system and particularly relates to dynamic optimization of a water treatment system by microprocessor control of additive addition in response to variations in electro chemical noise (RCN), changes in the linear polarization rate (LPR) and variations in the activity factor (AF).

BACKGROUND OF THE INVENTION

Corrosion of the metals making up the cooling water circulating system is of primary concern to owners and operators of such equipment. Of particular concern is the corrosion of the heat exchangers.

In industrial cooling systems, water from rivers, lakes, ponds, wells, wastewater treatment plant effluent etc., is employed as the cooling media for heat exchangers. These waters can contain a variety of either dissolved or suspended materials such as mineral salts, metals, organics, silt, mud etc. The cooling water from a heat exchanger is typically passed through a cooling tower, spray pond or evaporative system prior to discharge or reuse. In such systems, cooling is achieved by evaporating a portion of the water passing through the system. Because of the evaporation that takes place during the cooling, both dissolved and suspended solids concentrate.

The concentrating of various anionic ions such as chlorides and sulfates can increase the rate of corrosion of the metals making up the cooling system. This is especially true with the metals making up the heat exchangers that are experiencing higher temperatures due to heat transfer. Other contaminates such as hydrogen sulfide can also increase corrosion rates.

Mineral salts such as calcium and magnesium can induce scaling of the heat exchangers that reduces heat transfer. A scale common to many cooling systems is calcium carbonate. Additionally, scales such as calcium phosphate can also inhibit heat transfer as well as induce under deposit corrosion.

Deposit formation on heat exchangers also impedes heat transfer. For example, corrosion byproducts can form on the metal surface where a corrosion cell has formed. Alternatively, deposits from metal oxides, silt, mud, microbiological activity and process contamination can reduce the efficiency of heat transfer as well as increase corrosion.

Reducing the occurrence of corrosion, scaling, and deposition upon heat exchangers and associated cooling system equipment is essential to the efficient and economical operation of a cooling water system.

Excessive corrosion of the metallic surfaces can cause the premature failure of process equipment, necessitating down time for the replacement or repair of the equipment. Additionally, the buildup of corrosion products on the heat transfer surfaces impedes water flow and reduces heat transfer efficiency thereby limiting production or requiring downtime for cleaning.

To effectively apply inhibitors in dynamic conditions such as those described, the real-time performance of the inhibitor program is required. Undetected periods of high pitting rates and/or deposit formation can severely impede both performance and equipment life.

DESCRIPTION OF THE PRIOR ART

U.S. Pat. No. 4,648,043 teaches a computerized chemical application system for a water treatment system. A computer control senses the conductivity of a reference water flowing through the chemical introduction header and, based upon the differential conductivity and values relating conductivity to concentration for the water treatment liquid, precise control of the amount of water treatment liquid added is achieved.

U.S. Pat. No. 5,213,694 is directed toward a water treatment control system for treating cooling tower makeup water. The system utilizes a source of vacuum applied to an injector valve to draw chemicals from a holding tank into the make-up water.

SUMMARY OF THE INVENTION

The present invention describes an apparatus for the optimized control of various treatment chemicals (corrosion inhibitors and supporting treatments) applied for corrosion and/or deposit inhibition. The apparatus consist of a microprocessor system that controls inhibitor concentrations as a result of processed inputted data. The inputted data includes, but is not limited to, values consistent with the monitoring of Electrochemical Noise and Linear Polarization Rate, heat transfer, concentrations of water treatment chemistry, critical water chemistry parameters, and critical operational characteristics. Although the invention has been described with relation to water treatment processes, it is contemplated that the process can further be utilized for process side applications where electrolytes are present, but may be the solute rather than the solvent, e.g. processes dealing with hydrocarbons where water is only present at a very small percentage of the overall solution.

Accordingly, it is an objective of the instant invention to teach a device and a process for its use which can identify corrosion, particularly pitting corrosion, and institute steps to moderate such pitting conditions, under microprocessor control and in real-time thereby avoiding or substantially eliminating the initial stages of pit formation upon all affected metallic surfaces, particularly heat exchange surfaces.

It is an additional objective of the instant invention to integrate, under microprocessor control, the corrosion identifying process with a process for corrosion inhibition which can quickly suppress the corrosion cell(s) by making real-time adjustments to the inhibitor program.

It is yet an additional objective of the instant invention to teach a process for monitoring corrosion values for both electrochemical noise (ECN) and linear polarization rate (LPR) under heat transfer.

It is still an additional objective of the instant invention to teach a method of operation wherein the ECN and LPR values are processed to compare how the corrosion signals correlate.

Other objects and advantages of this invention will become apparent from the following description taken in conjunction with the accompanying drawings wherein are set forth, by way of illustration and example, certain embodiments of this invention. The drawings constitute a part of this specification and include exemplary embodiments of the present invention and illustrate various objects and features thereof.

DETAILED DESCRIPTION OF THE INVENTION

The present invention describes an apparatus for the optimized control of various treatment chemicals (inhibitors) applied for corrosion and/or deposit inhibition. The apparatus consists of a microprocessor system that controls inhibitor concentrations as a result of processed inputted data, coupled with the devices needed to collect said data. The inputted data includes, but is not limited to, values consistent with the monitoring of Electrochemical Noise and Linear Polarization Corrosion, heat transfer coefficients (fouling factors), concentrations of water treatment chemistry, critical water chemistry parameters, and critical operational characteristics.

Figure 1:
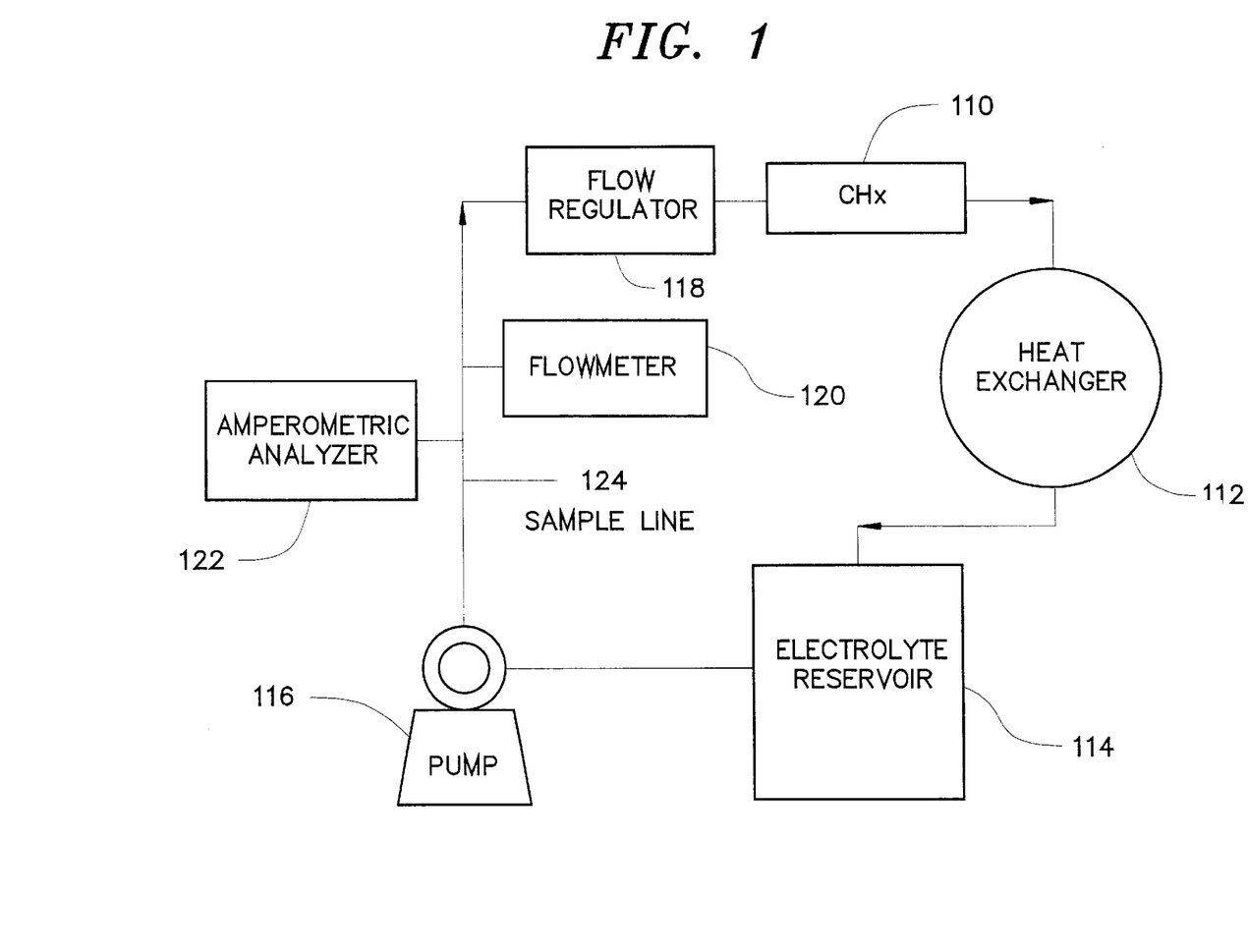
FIG. 1 is illustrative of a circulating system useful for conducting tests replicating a typical cooling water treatment application.

FIG. 1 is illustrative of a circulating system useful for conducting tests replicating a typical cooling water treatment application. With reference to FIG. 1, the instant device is comprised of a system that incorporates a MENTOR CHx heat transfer device (see FIG. 2) 110 that is made of the metallurgy to be tested. The metallurgy under heat transfer is in contact with an electrolyte which is pumped via pump 116 through a heat exchanger 112 through which electrolyte from electrolyte reservoir 114 is passed. The electrolyte flow rates and rates of heat transfer are adjusted to desired levels by adjusting flow regulator 118. A flowmeter 120 is in fluid communication for ease of adjustments. If added, the concentration of a passivator is measured using a standardized amperometric analyzer. A sample line 124 is optionally provided for convenience in withdrawing samples for testing.

Figure 2:
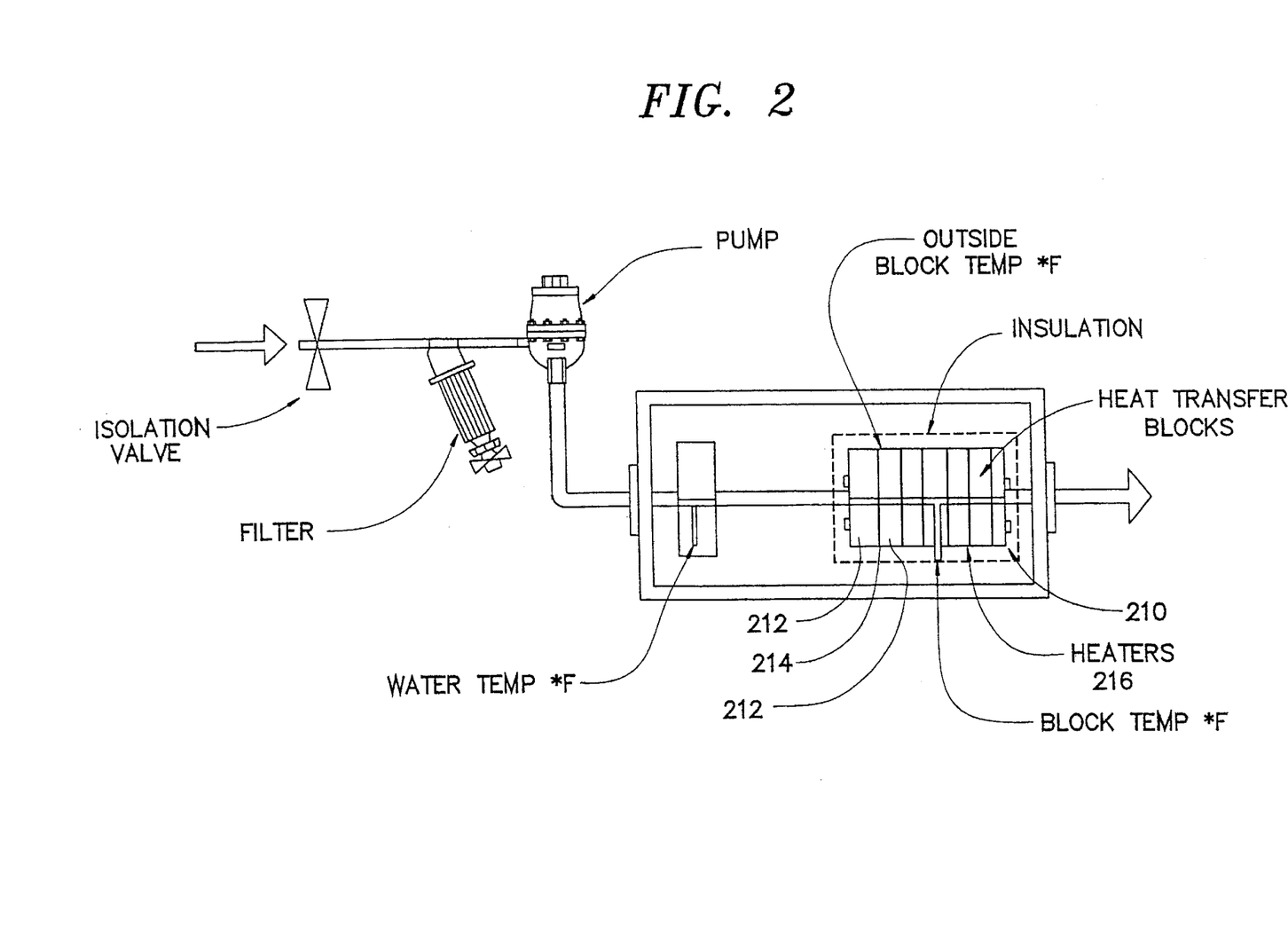
FIG. 2 illustrates a cross-sectional view of a MENTOR CHx device.

With reference to FIG. 2, a MENTOR CHx device is illustrated. For our testing we utilized the MENTOR-CHx system, available from Integriti Solutions Corp., to simulate the conditions associated with heat transfer equipment. Now with further reference to FIG. 2, a block 210 is comprised of a series of pieces of the desired metallurgy 212 that are joined with an insulating material 214 placed between each adjoining piece. This series of adjoined pieces will be designated the "block". A hole (not shown) is incorporated at some part of the construction process through which the electrolyte will contact the block. The metal pieces making up the block are equipped with appropriate sensing apparatus (not shown) for the sensing of ECN and LPR. Other sensing apparatus for determination of temperature gradients, heat transfer coefficients, etc. can be applied in a way that does not interfere with the performance of ECN and LPR sensing apparatus. The block is equipped with a device 216 to provide heat thru the block. The block is combined with other supporting equipment necessary for replicating the operational environment of the heat transfer equipment in question. This can include, but is not limited to, equipment necessary for replicating electrolyte flow rate, electrolyte chemical parameters, and skin temperature at the heat exchanger electrolyte interface, etc.

The process control parameters are adjusted and controlled to replicate the operational environment at the heat exchanger metal-electrolyte interface.

Figure 3:
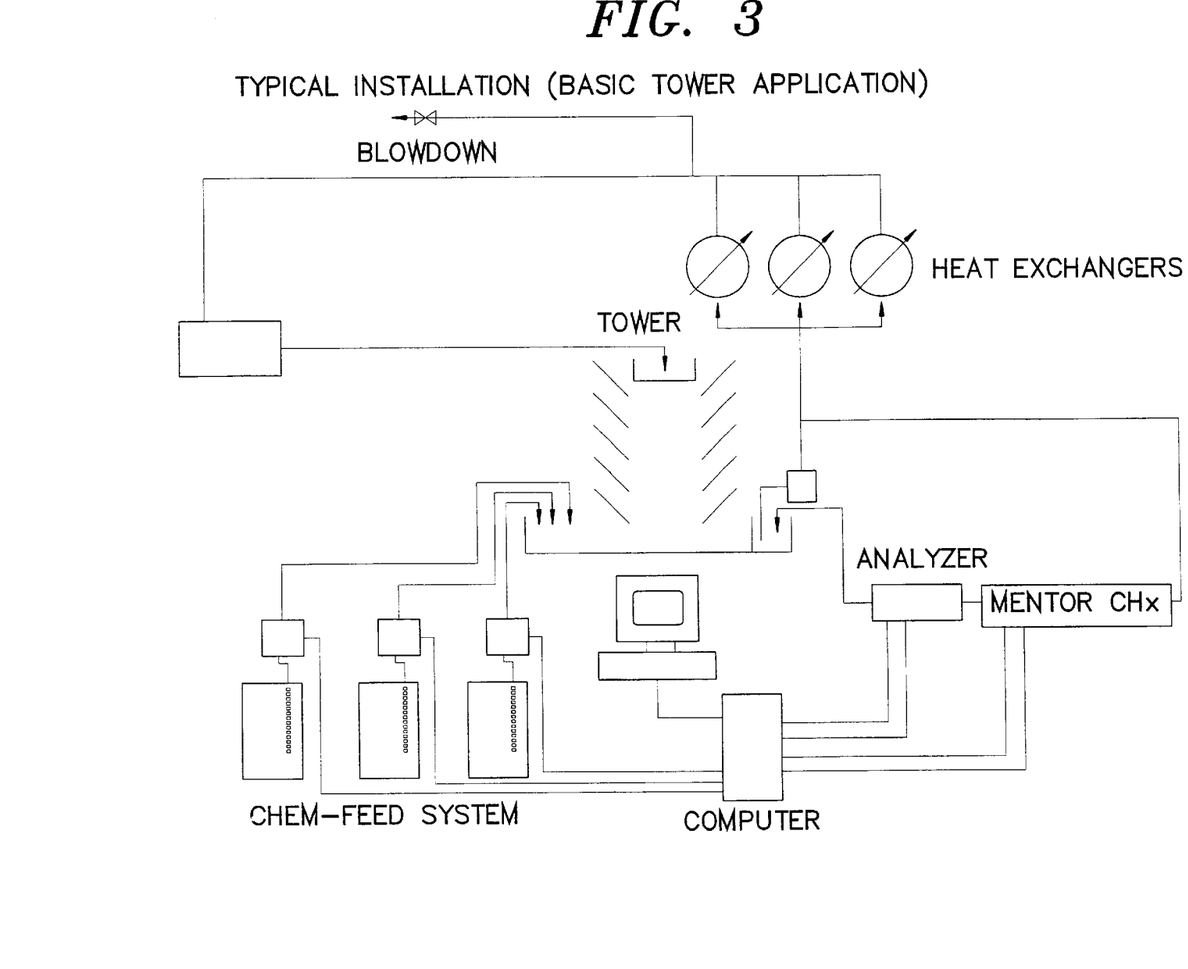
FIG. 3 is a flow diagram for a basic tower application using microprocessor control.

In accordance with FIG. 3, a typical installation is illustrated in the form of a basic tower application. A tower 310 receives the output of multiple heat exchangers 312 via flow line 314. Effluent from the tower is sampled vial sample line 316 which is in fluid communication with analyzers 318 and Mentor CHx 320. Data derived from both the analyzers and Mentor CHx units are transmitted to a central microprocessor 322 which may be analyzed via terminal 324. In accordance with the processing of data in microprocessor 322 utilizing programs based on applications experience, the processed data is utilized to optimize inhibitor concentrations by controlling flow from the chemical feed system 326 based on real-time performance. This provides the user with assured performance even under varying or upset conditions.

In the examples which follow, the operational conditions are adjusted to replicate the operational environment at the heat exchanger metal-electrolyte interface in question.

EXAMPLES

The ability to measure the performance of water treatment programs is essential to optimizing the addition and concentration of various corrosion and deposit control treatments. When program performance can be quantified, optimization of treatment(s) can be made in real-time to maintain system integrity even in upset conditions. This level of control and performance has remained somewhat elusive for water treatment professional.

FIG. 1 illustrates the circulating system used to conduct the test. All testing was performed at a skin temperature of 144° F. using 1010 carbon steel. Flowrate was regulated at 3.8 gpm.

Example 1

A passivating agent was added to the electrolyte to induce passivation of the electrodes. The electrolyte was circulated through the CHx until steady state was reached.

The concentration of passivator was measured using both a standardized amperometric sensor, and wet chemistry methodology. The concentration needed to sustain the passive condition was maintained throughout the testing period.

Figure 4:
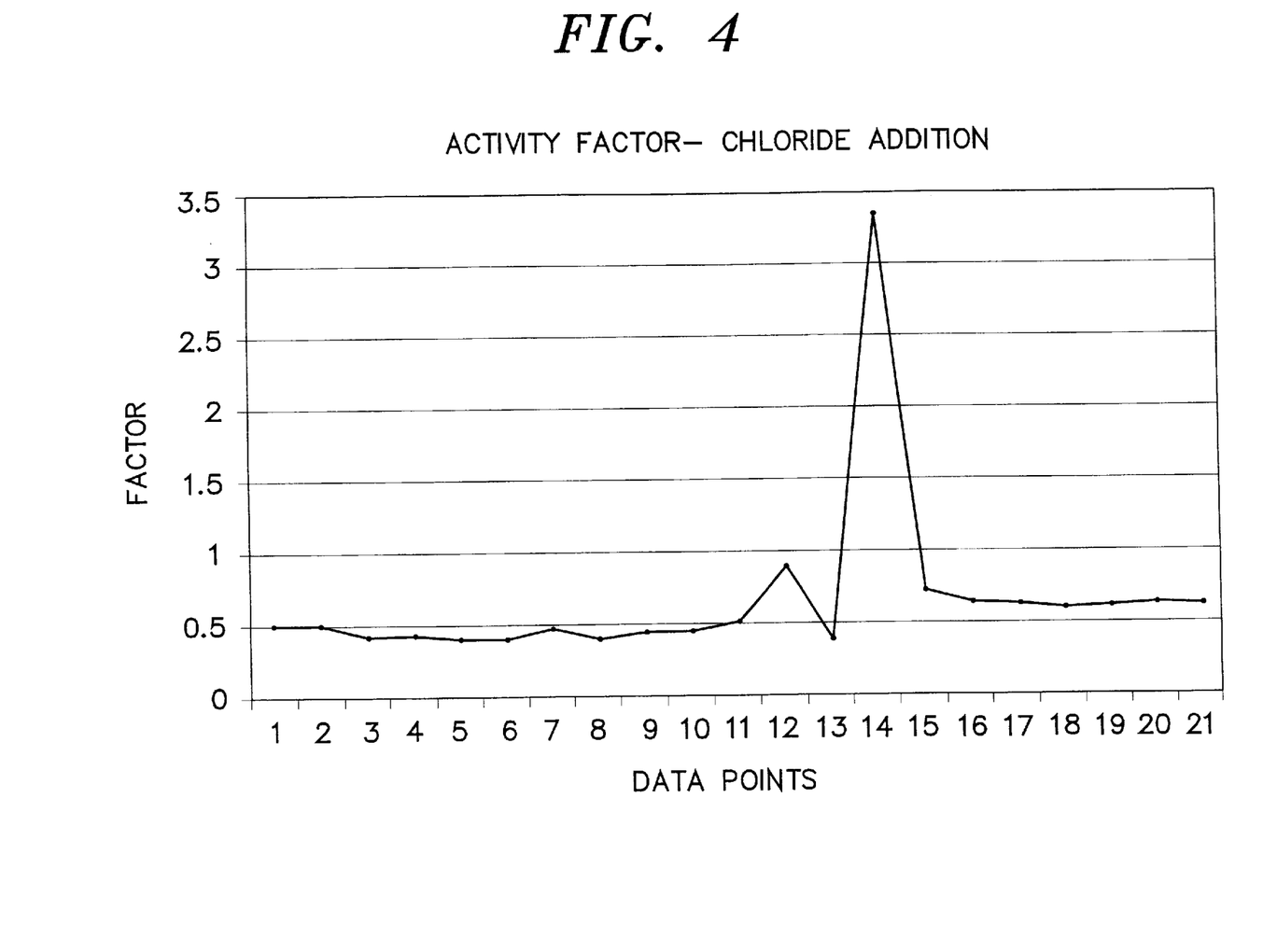
FIG. 4 is a graphical representation of Activity Factor with Chloride Addition.
Figure 5:
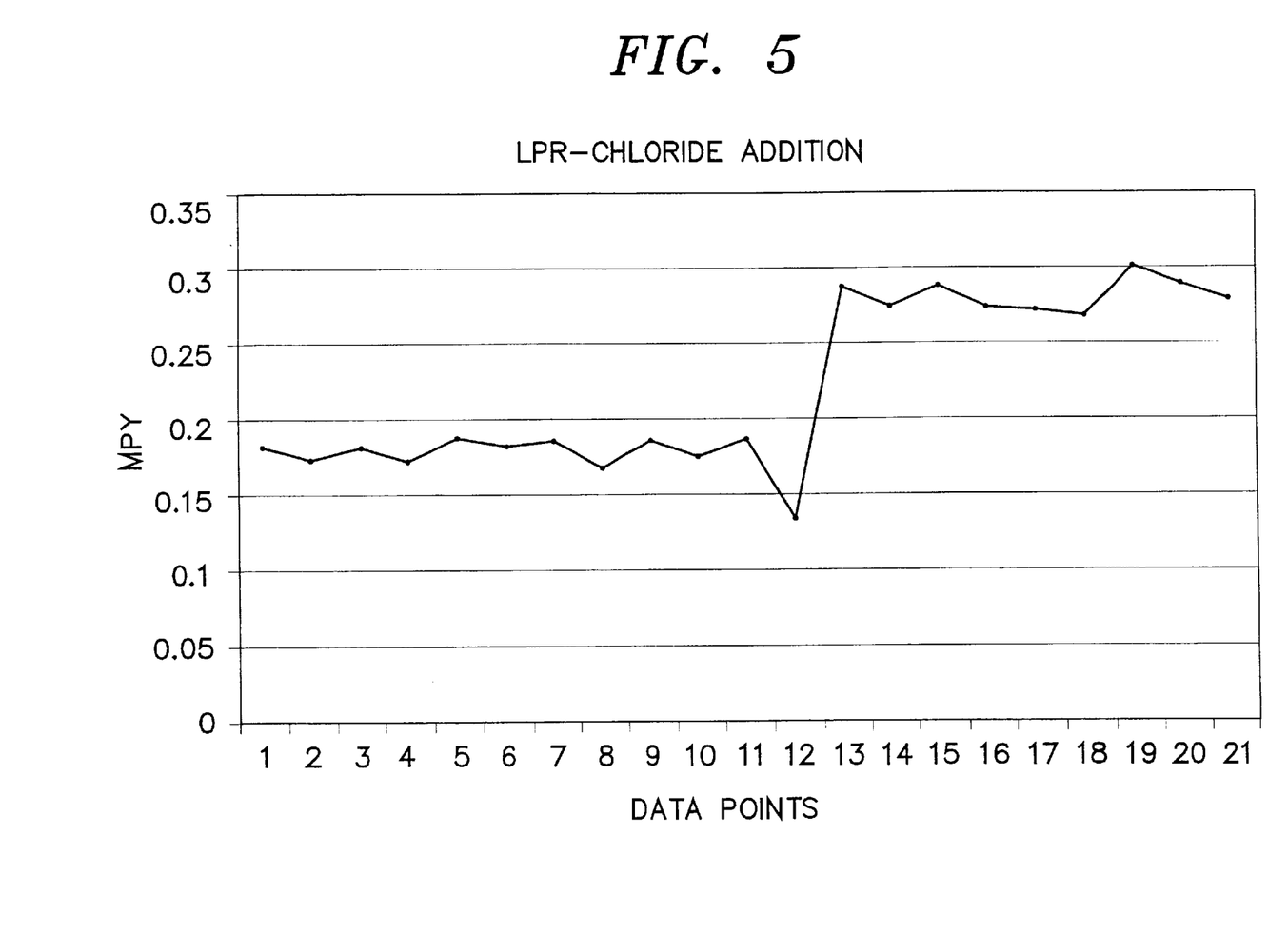
FIG. 5 is a graphical representation of Linear Polarization Rate with Chloride Addition.
Figure 6:
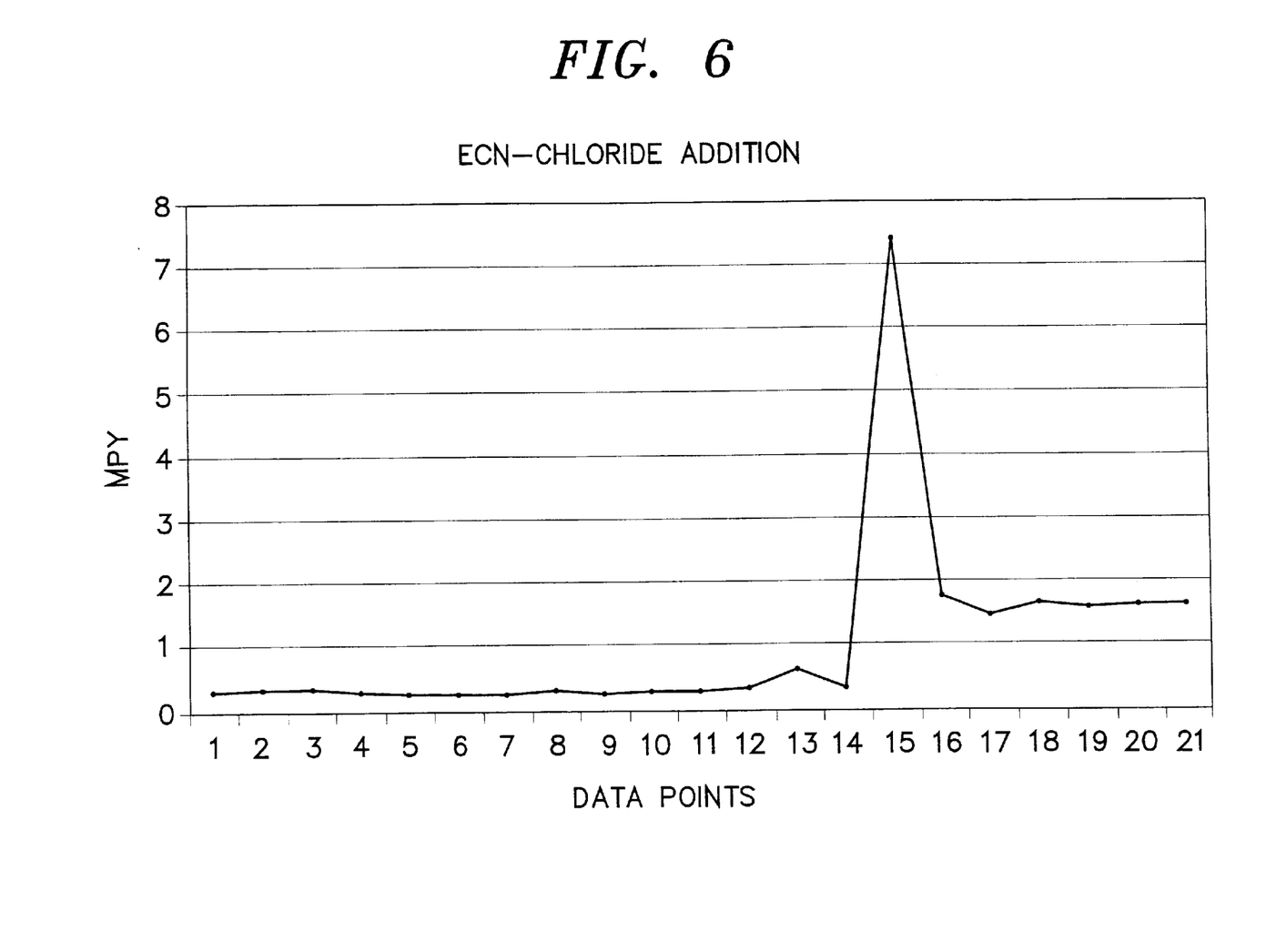
FIG. 6 is a graphical representation of Electrochemical Noise with Chloride Addition.

Referring to FIGS. 4–6, data points from 1–11 illustrate a steady state condition. 100 ppm of Chlorides as Cl- was added to the electrolyte to represent an upset condition. The "Activity Factor" (AF) is calculated using the equation:

$$AF = \sigma_i / i_{rms}$$

where $\sigma_i$ is the standard deviation of the electrochemical current noise data, and $i_{rms}$ is the root mean square of the electrochemical current noise.

The AF detects changes in current and highlights the deviation from the steady state condition. However, it alone does not indicate the nature of corrosion since increased oxidation potential of the electrolyte such as with the addition of passivating agents will increase current, and induce an increase in AF.

Because the data collected using electrochemical noise (ECN) corrosion techniques is non-intrusive, the corrosion data is clean of interferences like the applied potential technique linear polarization. For this reason, the data is related to those mechanisms directly involved with corrosion. When ECN electrodes are exposed to either a pitting or passivating environment, the electrochemical noise current increases, thereby indicating an increase in AF, and typically a corresponding increase in ECN corrosion rate.

LPR is an intrusive technique that applies a potential that polarizes the electrode. Because LPR is an intrusive technique for measuring corrosion, the technique is limited to measuring changes in current from the steady state condition (polarized state). When the LPR electrode is polarized, then exposed to a pitting environment, the initial measured corrosion rate decreases. However, when LPR electrodes are exposed to a passive environment, the initial measured corrosion rate increases. When the LPR electrode is polarized, then depolarized as a result of exposure to a pitting environment, the initial corrosion rate decreases. However, when LPR electrodes are polarized and then depolarized while being exposed to a passive environment, the initial corrosion rate increases. This phenomena is a result of the difference in driving force that induces the flow of current. In the first case, the driving force is the formation of a large cathode around the small anode (pit). In the later case, the driving force is the high potential passivating agent in the electrolyte.

When a large cathode forms, the large cathodic area is highly polarized and exhibits an increased resistance. Because LPR corrosion rates are directly related to resistance by the equation:

$$MPY = K/Rp \qquad (A)$$

where:
  K is the Stern-Geary constant
    (generally available from the literature and dependent upon the metal/environment combination)
  A is the electrode surface area
  Rp is the polarization resistance
where $Rp = \Delta E/\Delta I$ (change in potential/change in current).

It has been discovered that the characteristics of LPR can be used in combination with the true readings of ECN to determine the nature of corrosion. Once the true nature of corrosion is determined, appropriate selection and addition of corrosion inhibitors can be applied in real-time to prevent the propagation of localized corrosion.

Although the examples herein compare LPR corrosion rate to AF, the instant invention contemplates similar comparisons which could be made, e.g. by comparing electrochemical noise corrosion rate versus LPR corrosion rate or comparing LPR resistance versus AF or ECN corrosion rate.

As the resistance increases, corrosion rate decreases. Therefore, when LPR corrosion rate is correlated with AF, the signals diverge with the onset of pitting corrosion.

With the increased AF at data point 12, data point 12 for AF and LPR was correlated which showed a dramatic divergence in signal. This divergence indicates the initiation of pitting corrosion.

After detection of the pitting corrosion, 50ppm of passivating agent was added to the electrolyte, which induced the electrodes to re-polarize by data point 15.

The real-time monitoring and evaluation of corrosion data proved a valuable tool in inhibiting the corrosion in its earliest stage of development.

Utilizing microprocessor control, the propagation of pitting was averted by combining: data generated using ECN and LPR corrosion measuring techniques, real-time identification of both increased corrosion activity (AF) and nature of corrosion (correlation of AF with LPR), selection of the appropriate corrosion inhibitor(s) and dosage(s), and a method of chemical(s) delivery to the electrolyte.

Preparation for Example 2

To achieve a skin temperature of 144° F., the CHx required $65.6412 BTU/hr.ft^2 \times 10^3$. This was recorded as the baseline heat transfer under steady state conditions. The CHx was then exposed to a corrosive electrolyte under stagnant conditions for several days.

When the circulation pump was activated, red water was observed leaving the CHx. After allowing the system to reach steady state under heat transfer, the rate of heat transfer required to achieve a skin temperature of 144° F. was monitored and recorded as $52.8664 BTU/hr.ft^2 \times 10^3$.

The lower heat transfer value indicates a 19.46% reduction in heat transfer efficiency due to the presence of corrosion byproducts (ferric oxide). Based on the heat transfer data, it is apparent heat transfer was substantially impaired. In applications utilizing heat transfer equipment a 19.46% reduction in heat transfers could substantially impact production. Effective removal of the deposit(s) while under heat transfer is desired. Difficulties exist in determining the: type of cleaning agent, concentration, and contact time.

Severe corrosion damage resulting from excessive concentrations, contact times, or poor selection of cleaners and/or corrosion inhibitors are common. The ability to optimize the selection, concentration and contact time by utilizing a microprocessor to effect real-time control would allow for optimum recovery of heat transfer while maintaining system integrity.

Example 2

Figure 8:
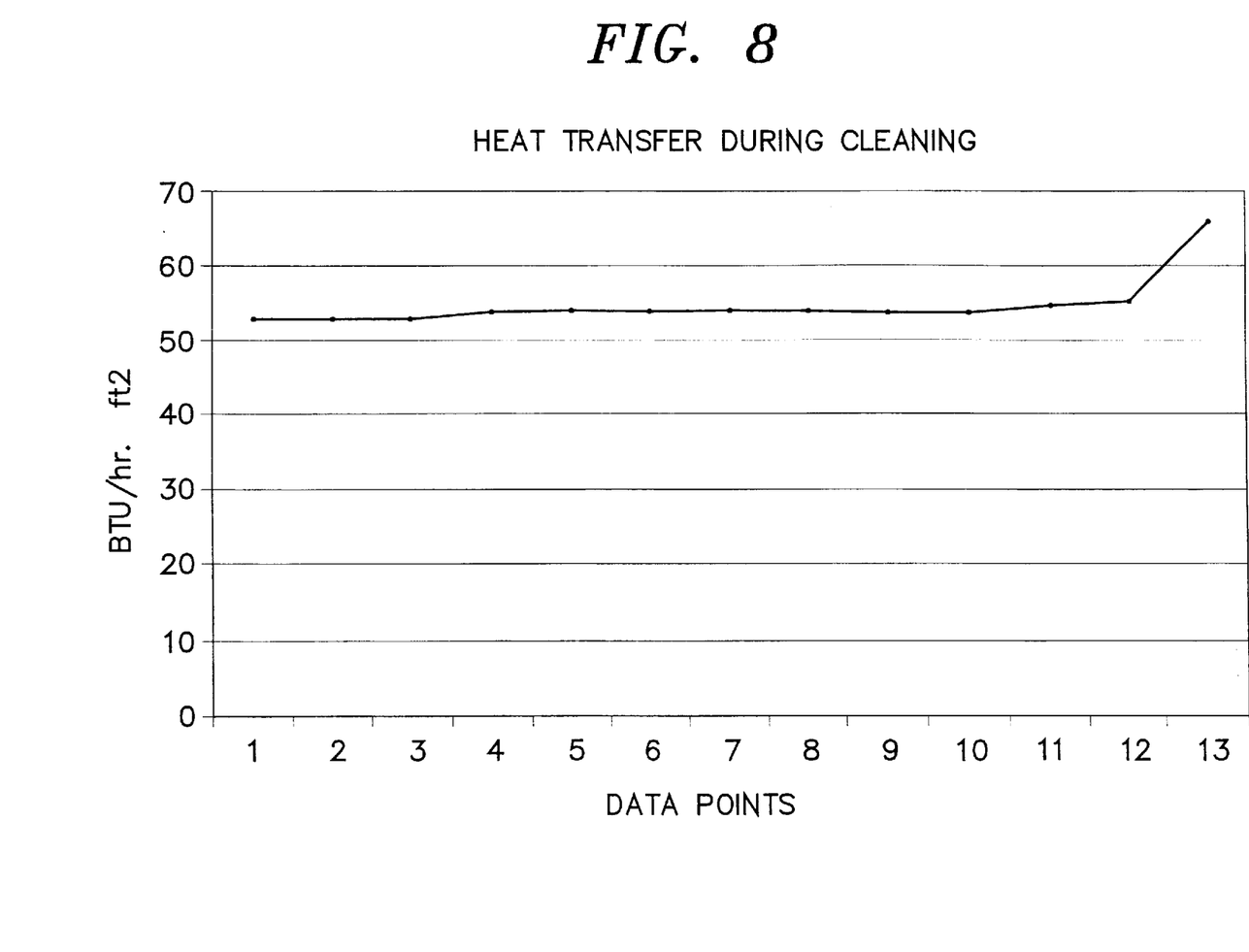
FIG. 8 is a graphical representation of Heath Transfer During Cleaning.

The electrolyte was initially treated with 1000 ppm of a peroxycitric acid solution made from a 2:1 actives weight ration of hydrogen peroxide and citric acid. FIG. 8 illustrates the heat transfer increased (data point 4) while ECN showed a corresponding rise in corrosion rate. ECN corrosion rates then dramatically drop (data point 5), followed by the onset of a passivesteady state condition (data points 8–13).

Figure 7:
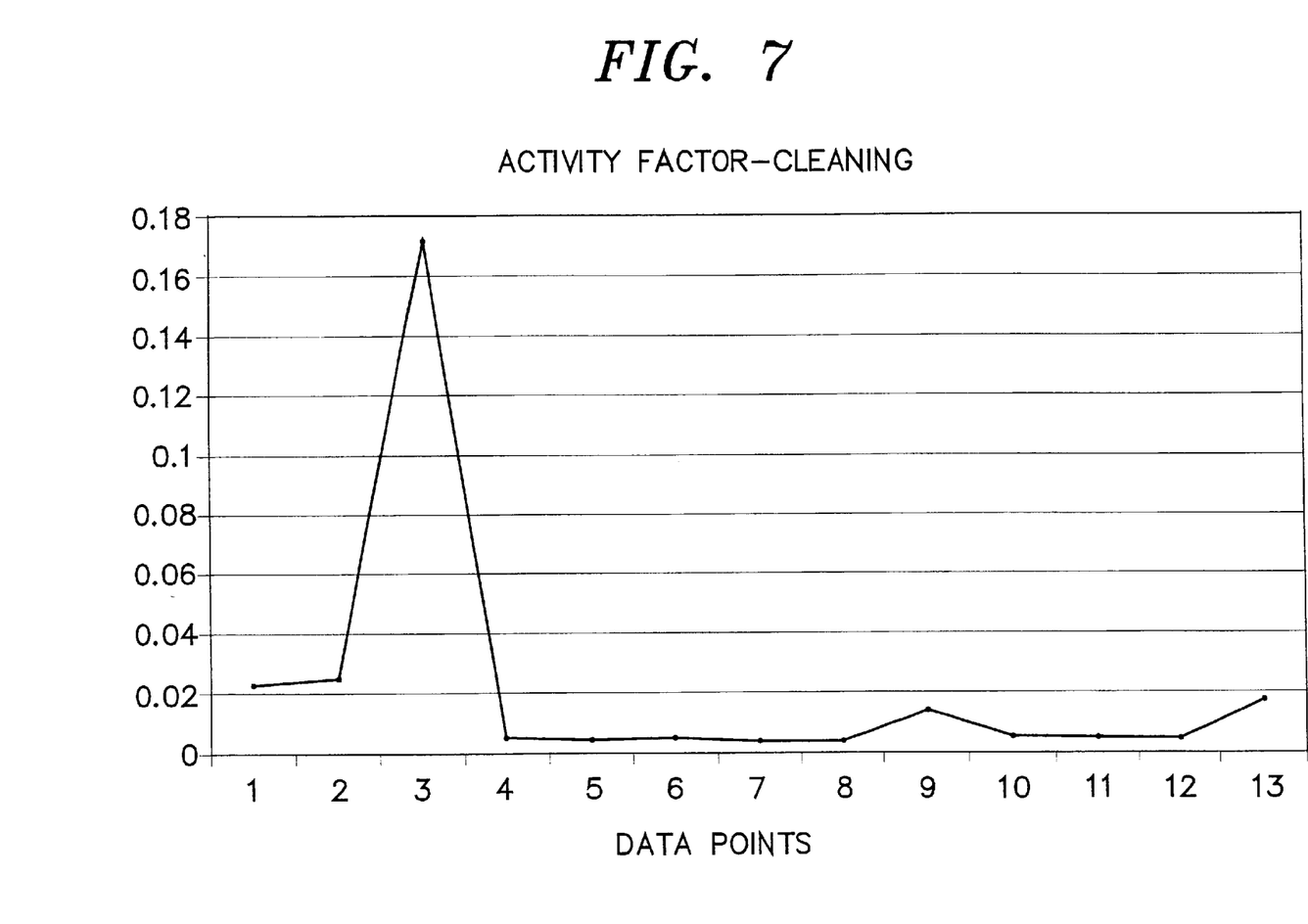
FIG. 7 is a graphical representation of Activity Factor During Cleaning.

By data point 12, heat transfer recovered 22% of the lost heat transfer resulting from the removal of much of the insulating ferrous oxide. Data point 13 shows the affects of adding 1000 ppm of HCl (based on active(s)). Heat transfer is completely restored while maintaining unprecedented control of ECN corrosion rate and Activity Factor (FIG. 7).

100% recovery of heat transfer was achieved by removing the deposit while avoiding severe corrosion, especially pitting corrosion. Conclusions:

Using real-time condition monitoring, real-time adjustments under microprocessor control can be made to the electrolyte treatment thereby minimizing the detrimental affects, as well as reverse these effects (as in the case of deposit removal example). Implementation of this process control system would improve any corrosion and/or deposit control application where the electrolyte induces corrosion and/or deposits on metal surfaces, especially those applications where heat transfer is involved.

Real-time adjustments substantially improve equipment life while maximizing operational performance even under upset conditions. Incorporating artificial intelligence with this control technology would allow for proactive compensation effective to moderate corrosive conditions before the symptoms arise. Based on real-time analysis of incoming data for corrosion, heat transfer, water chemistry, operational conditions etc., adjustments in treatment(s) can be made based on analysis of historical data and events.

It is to be understood that while a certain form of the invention is illustrated, it is not to be limited to the specific form or arrangement of parts herein described and shown. It will be apparent to those skilled in the art that various changes may be made without departing from the scope of the invention and the invention is not to be considered limited to what is shown and described in the specification and drawings.

What is claimed is:

1. A method for detecting onset of localized pitting corrosion comprising:

measuring electrochemical noise (ECN);

measuring linear polarization corrosion rate (LPR);

calculating activity factor (AF) according to the equation:

$$AF = \sigma_i / i_{rms}$$

where $\sigma_i$ represents standard deviation of the electrochemical current noise rate, and $i_{rms}$ is the root mean square of the electrochemical current noise;

performing a real-time evaluation of changes in AF values to changes in LPR corrosion rate values, wherein divergence in said values is indicative of the onset of localized pitting corrosion, communicating variations in measured and calculated values of ECN, LPR and AF to a microprocessor control system;

transmitting instructions to a feed system constructed and arranged for dosing at least one additive in an amount effective to moderate corrosion; and dosing required amounts of said at least one additive.

2. A method in accordance with claim 1 further including:

microprocessor control of real-time selection and addition of corrosion inhibitors and supporting treatments of a type and in an amount effective to prevent or suppress the propagation of said localized pitting corrosion.

3. The process in accordance with claim 1 wherein said microprocessor based control system processes inputted data and regulates water treatment chemical concentration based upon real-time and historical performance.

4. The process of claim 1 wherein said measured, calculated and historical values are selected from the group consisting of values consistent with the monitoring of ECN, LPR, AF, heat transfer, concentrations of water treatment chemistry, water chemistry parameters, and operational characteristics.

5. A process for detecting and forecasting the onset of localized pitting corrosion at the metal-electrolyte interface of a heat exchanger comprising:

replicating the operational environment at the heat exchanger metal-electrolyte interface;

measuring electrochemical noise (ECN);

measuring linear polarization corrosion rate (LPR);

calculating activity factor (AF) according to the equation:

$$AF = \sigma_i / i_{rms}$$

where $\sigma_i$ represents standard deviation of the electrochemical current noise rate, and $i_{rms}$ is the root mean square of the electrochemical current noise;

performing a real-time evaluation of changes in AF values to changes in LPR corrosion rate values; wherein divergence in said values is indicative of the onset of localized pitting corrosion within said heat exchanger;

communicating variations in measured and calculated values of ECN, LPR and AF to a microprocessor;

transmitting instructions to a feed system constructed and arranged for dosing at least one additive in an amount effective to moderate corrosion; and dosing required amounts of said at least one additive.

6. A method in accordance with claim 5 further including:

microprocessor control of real-time selection and addition of corrosion inhibitors of a type and in an amount effective to prevent or suppress the propagation of said localized pitting corrosion.

7. The process in accordance with claim 5 wherein said microprocessor based control system processes inputted data and regulates water treatment chemical concentration based upon real-time performance, or trends in the data that historically impeded performance.

8. The process of claim 5 wherein said measured, calculated and historical values are selected from the group consisting of values consistent with the monitoring of ECN, LPR, AF, heat transfer, concentrations of water treatment chemistry, water chemistry parameters, and operational characteristics.

* * * * *